(12) United States Patent
Rao et al.

(10) Patent No.: US 9,938,297 B2
(45) Date of Patent: Apr. 10, 2018

(54) PROCESS FOR THE SYNTHESIS OF EVEROLIMUS AND INTERMEDIATES THEREOF

(71) Applicant: Cipla Limited, Mumbai (IN)

(72) Inventors: Dharmaraj Ramachandra Rao, Mumbai (IN); Geena Malhotra, Mumbai (IN); Venkata Srinivas Pullela, Bangalore (IN); Vinod Parameshwaran Acharya, Mumbai (IN)

(73) Assignee: Cipla Limited, Mumbia (IN)

( * ) Notice: Subject to any disclaimer, the term of this patent is extended or adjusted under 35 U.S.C. 154(b) by 0 days.

(21) Appl. No.: 15/501,416

(22) PCT Filed: Aug. 4, 2015

(86) PCT No.: PCT/GB2015/052248
§ 371 (c)(1),
(2) Date: Feb. 2, 2017

(87) PCT Pub. No.: WO2016/020664
PCT Pub. Date: Feb. 11, 2016

(65) Prior Publication Data
US 2017/0217988 A1    Aug. 3, 2017

(30) Foreign Application Priority Data

Aug. 4, 2014 (IN) .......................... 2499/MUM/2014

(51) Int. Cl.
*C07D 498/18* (2006.01)
(52) U.S. Cl.
CPC .................. *C07D 498/18* (2013.01)
(58) Field of Classification Search
CPC .................................................. C07D 498/18
See application file for complete search history.

(56) References Cited

U.S. PATENT DOCUMENTS 5,665,772 A    9/1997  Cottens et al.

FOREIGN PATENT DOCUMENTS

| CN | 103788114 A | 5/2014 |
|----|----|----|
| EP | 1518517 A2 | 3/2005 |
| IN | 2499MUM2014 | 8/2014 |
| WO | 2012103959 A1 | 8/2012 |
| WO | 2012103960 A1 | 8/2012 |
| WO | 2016020664 A1 | 2/2016 |

OTHER PUBLICATIONS

Foreign communication from the priority application—International Search Report and Written Opinion of the International Searching Authority of PCT/GB2015/052248 dated Oct. 7, 2015, 9 pages.
Moenius, Thomas, et al., "Tritium labelling of RAD001—a new rapamycin derivative," Journal of Labelled Compounds and Radiopharmaceuticals, Feb. 2000, pp. 113-120, vol. 43, No. 2, John Wiley & Sons, Ltd.

*Primary Examiner* — Timothy R Rozof
(74) *Attorney, Agent, or Firm* — Conley Rose, P.C.; Rodney B. Carroll

(57) ABSTRACT

The present invention relates to a novel process for the synthesis of everolimus of formula (I):

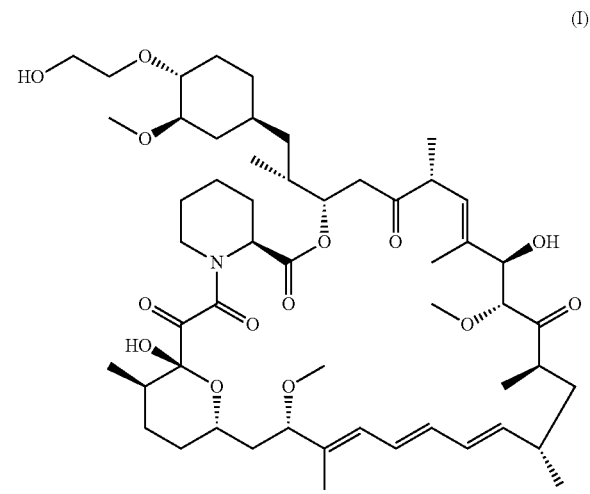

and intermediates thereof.

21 Claims, No Drawings

PROCESS FOR THE SYNTHESIS OF EVEROLIMUS AND INTERMEDIATES THEREOF

CROSS REFERENCE TO RELATED APPLICATIONS

This application is a filing under 35 U.S.C. 371 of International Application No. PCT/GB2015/052248 filed Aug. 4, 2015, entitled "Process of the Synthesis of Everolimus and Intermediates Thereof" which claims priority to Indian Patent Application No. 2499/MUM/2014 filed Aug. 4, 2014, which applications are incorporated by reference herein in their entirety.

FIELD OF THE INVENTION

The present invention relates to the synthesis of everolimus and intermediates thereof.

BACKGROUND OF THE INVENTION

Everolimus (RAD-001) is the 40-O-(2-hydroxyethyl)-rapamycin of formula (I),

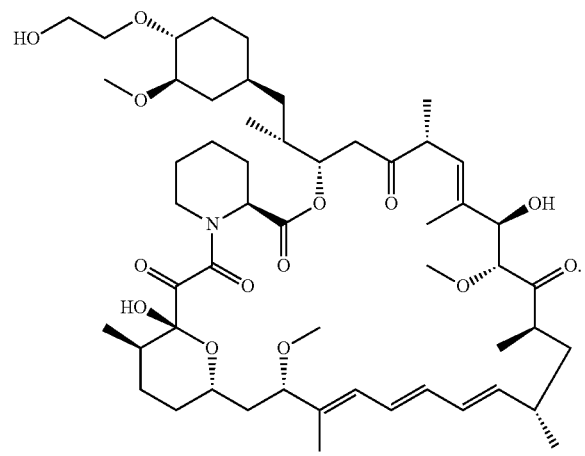 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

It is a derivative of sirolimus of formula (III),

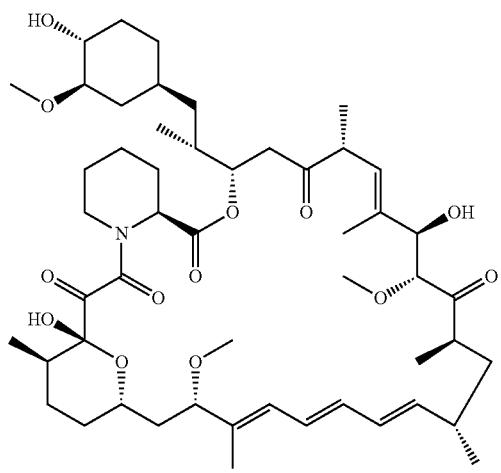 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

and works similarly to sirolimus as an inhibitor of mammalian target of rapamycin (mTOR). Everolimus is currently used as an immunosuppressant to prevent rejection of organ transplants and treatment of renal cell cancer and other tumours. It is marketed by Novartis under the tradenames Zortress™ (USA) and Certican™ (Europe and other countries) in transplantation medicine, and Afinitor™ in oncology.

Trisubstituted silyloxyethyltrifluoromethane sulfonates (triflates) of the general formula (IV),

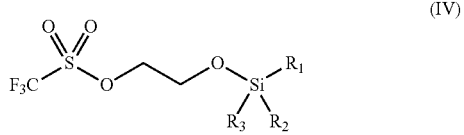

wherein $R_1$, $R_2$, $R_3$ are independently a straight or branched alkyl group, for example $C_1$-$C_{10}$ alkyl, and/or an aryl group, for example a phenyl group, are important intermediates useful in the synthesis of everolimus.

Everolimus and its process for manufacture using the intermediate 2-(t-butyldimethyl silyl) oxyethyl triflate of formula (IVA),

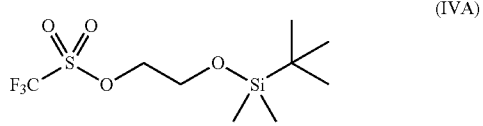 [SMILES: CC(C)(C)[Si](C)(C)OCCOS(=O)(=O)C(F)(F)F]

was first described in U.S. Pat. No. 5,665,772. The overall reaction is depicted in Scheme I.

Scheme I
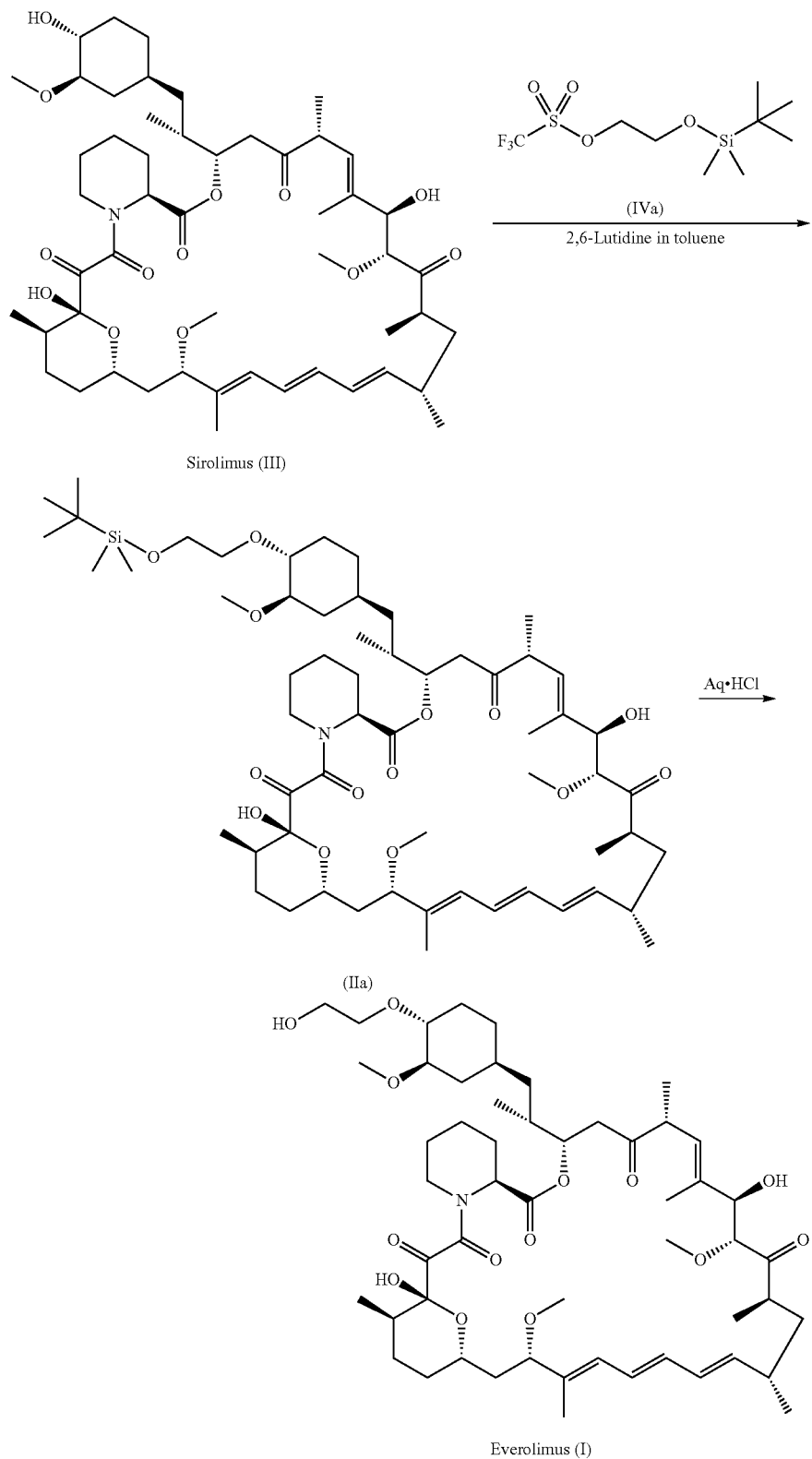
For the synthesis, firstly sirolimus of formula (III) and 2-(t-butyldimethylsilyl)oxyethyl triflate of formula (IVA) are reacted in the presence of 2,6-Lutidine in toluene at around 60° C. to obtain the corresponding 40-O-[2-(t-butyldimethylsilyl)oxy]ethyl rapamycin of formula (IIa), which is then deprotected in aqueous hydrochloric acid and converted into crude everolimus [40-O-(2-Hydroxy)ethyl rapamycin] of formula (I).

However, this process results in the formation of impure everolimus, which requires purification by column chromatography. The process results in very poor overall yield and purity and thereby the process is not suitable for the commercial scale production of everolimus.

Moenius et al. (I. Labelled Cpd. Radiopharm. 43, 113-120 (2000) have disclosed a process to prepare C-14 labelled everolimus using the diphenyltert-butylsilyloxy-protective group of formula (IV B),

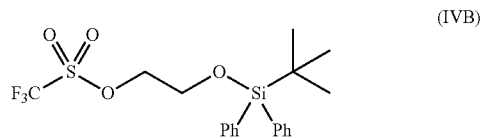 [SMILES: CC(C)(C)[Si](OCCOS(=O)(=O)C(F)(F)F)(c1ccccc1)c1ccccc1]
(IVB)

as the alkylation agent. The overall yield reported was 25%.

International patent application, publication number WO 2012/103960 discloses the preparation of everolimus using the alkylating agent 2-((2,3-dimethylbut-2-yl)dimethylsilyloxy)ethyl triflate of formula (IVC),

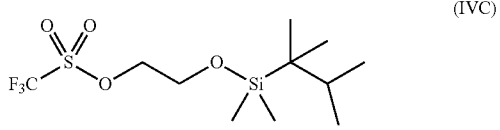 [SMILES: CC(C)C(C)(C)[Si](C)(C)OCCOS(=O)(=O)C(F)(F)F]
(IVC)

wherein the overall yield reported is 52.54%. The process involves a derivatization method based on the reaction of the triflate (IV) with a derivatization agent, which preferably is a secondary aromatic amine, typically N-methylaniline.

International patent application, publication number WO 2012/103959 also discloses the preparation of everolimus using the alkylating agent of formula (IVC). The process is based on a reaction of rapamycin with the compound of formula (IVC) in the presence of a base (such as an aliphatic tertiary amine) to form 40-O-2-(t-hexyldimethylsiloxy)ethylrapamycin, which is subsequently deprotected under acidic conditions to obtain everolimus.

European Patent Number 1518517B discloses a process for the preparation of everolimus which employs the triflate compound of formula (IVA), 2-(t-butyldimethyl silyl) oxyethyl triflate. The disclosed process for preparing the compound of formula (IVA) involves a flash chromatography purification step.

The compounds of formula (IV) are key intermediates in the synthesis of everolimus. However, they are highly reactive and also very unstable, and their use often results in decomposition during reaction with sirolimus. This is reflected by the fact that the yields of the reaction with sirolimus are very low and the compounds of formula (IV) are charged in high molar extent. Thus it is desirable to develop a process to stabilize compounds of formula (IV) without loss of reactivity.

OBJECTS OF THE INVENTION

The object of the present invention is to provide an alternative process for preparing everolimus and intermediates thereof.

Yet another object of the present invention is to provide a process which is simple, economical and suitable for industrial scale up.

SUMMARY OF THE INVENTION

Accordingly, the present invention relates to a process of preparing everolimus of formula (I),

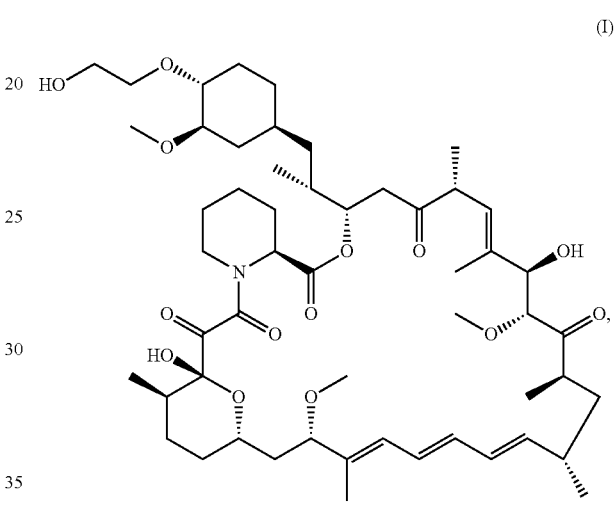
(I)

which process comprises the steps of:
either,
a) reacting a 2-([trisubstituted]silyloxy)ethanol compound of formula (V),

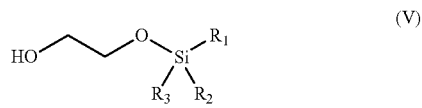
(V)

with trifluoromethane sulfonic acid or an activated derivative thereof, in the presence of a base and an organic solvent, to form a trisubstituted silyloxyethyltrifluoromethane sulfonate (triflate) compound of formula (IV),

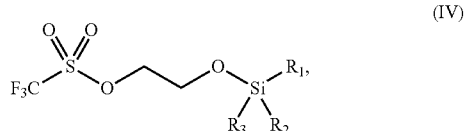
(IV)

wherein, $R_1$, $R_2$ and $R_3$, which may be the same or different, are independently a straight or branched chain lower alkyl group and/or an aryl group;

b) mixing sirolimus of formula (III),

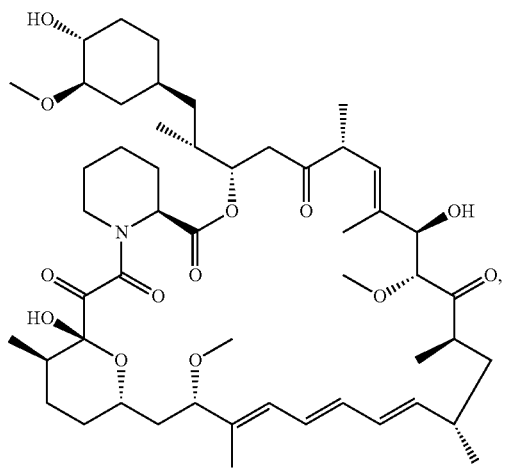

with a metal salt in an organic solvent; and c) admixing the solution containing the triflate compound of formula (IV) obtained in step a) with the reaction mixture obtained in step b) to obtain protected everolimus of formula (II),

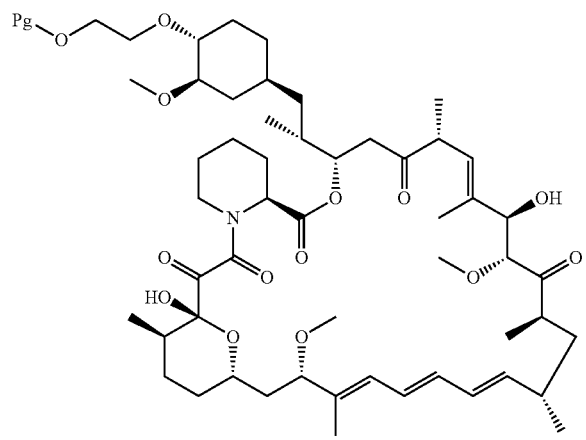

wherein, Pg is a silyl protecting group "—SiR$_1$R$_2$R$_3$" derived from the triflate compound of formula (IV);

or, d) reacting a 2-([trisubstituted]silyloxy)ethanol compound of formula (V):

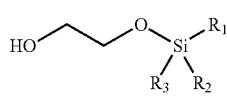

with trifluoromethane sulfonic acid and/or an activated derivative thereof, in the presence of a base and an organic solvent, to form a solution comprising a trisubstituted silyloxyethyltrifluoromethane sulfonate (triflate) compound of formula (IV);

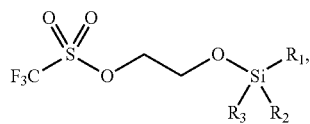

wherein R$_1$, R$_2$ and R$_3$, which may be the same of different, are independently a straight or branched chain lower alkyl group and/or an aryl group;

e) reducing the volume of the solution comprising the compound of formula (IV) obtained in step d), without completely removing all of the organic solvent present;

f) reacting sirolimus of formula (III),

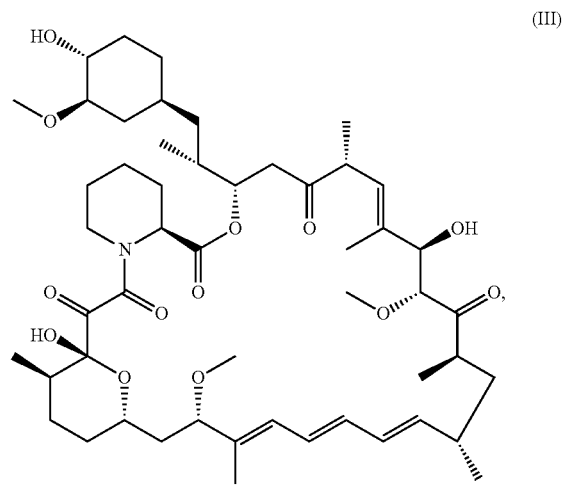 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

with the reaction mixture obtained in step e), in the presence of an organic solvent and a base to obtain protected everolimus of formula (II),

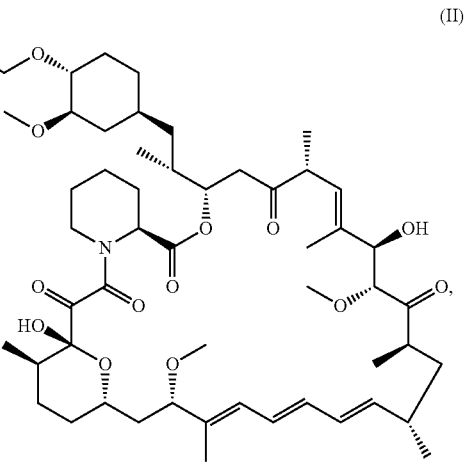

wherein, Pg is a silyl protecting group "—SiR$_1$R$_2$R$_3$" derived from the triflate compound of formula (IV);

and following step c) or step f), g) optionally purifying the protected everolimus of formula (II); and h) deprotecting compound (II) to obtain everolimus of formula (I).

DETAILED DESCRIPTION OF THE INVENTION

In one aspect of the present invention, there is provided the synthesis of everolimus of formula (I), as depicted below in reaction Scheme II.

Scheme II

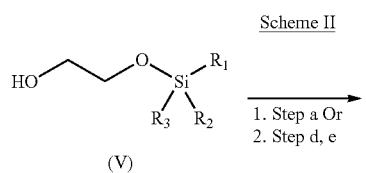

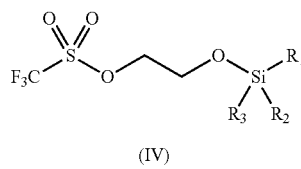

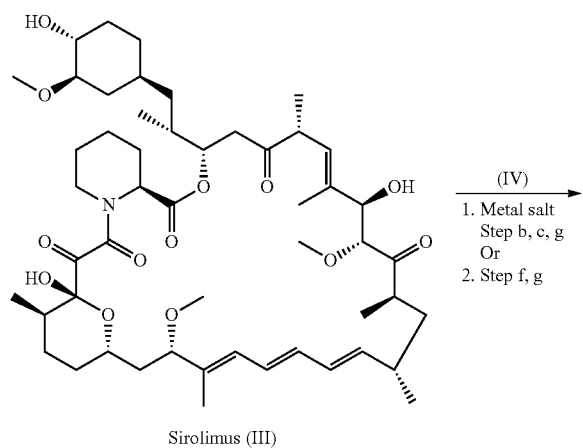

Sirolimus (III)

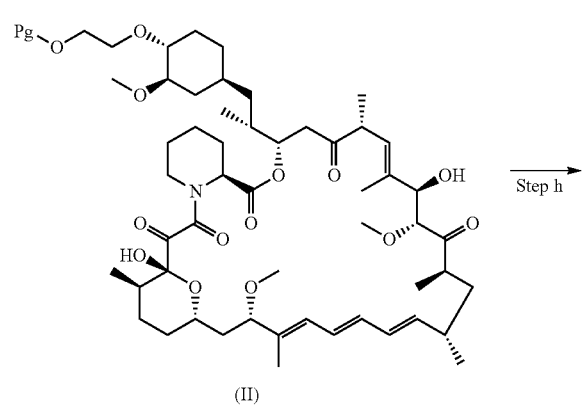

(II)

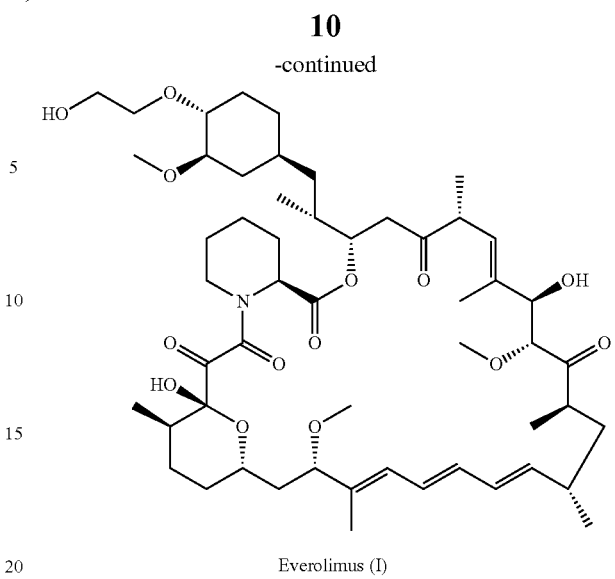

Everolimus (I)

wherein, $R_1$, $R_2$ and $R_3$, which may be the same or different, are independently a lower alkyl group and/or an aryl group. Preferably, the lower alkyl group is a straight or branched chain $C_1$-$C_6$ alkyl group, such as methyl, ethyl, propyl, butyl, pentyl or hexyl. Preferably, the aryl group is a phenyl group.

The substituent "Pg" in Scheme II is a silyl protecting group "—$SiR_1R_2R_3$" derived from the triflate compound of formula (IV) and is preferably selected from t-butyldimethylsilyl, diphenyl-tert-butylsilyl, hexyldimethylsilyl and 2-{4-[(triisopropylsilyl)] phenoxy}.

In step a) of the process of the present invention, a 2-([trisubstituted]silyloxy)ethanol compound of formula (V) is reacted with trifluoromethane sulfonic acid or an activated derivative thereof in the presence of a base and an organic solvent, to form a trisubstituted silyloxyethyltrifluoromethane sulfonate (triflate) compound of formula (IV). A preferred activated derivative of trifluoromethane sulfonic acid is trifluoromethane sulfonic anhydride.

Preferably, the 2-([trisubstituted]silyloxy)ethanol compound of formula (V) is selected from the group consisting of:

t-butyldimethylsilyloxy ethanol (VA), diphenyl-tert-butylsilyloxy ethanol (VB), and hexyldimethylsilyloxy ethanol (VC),

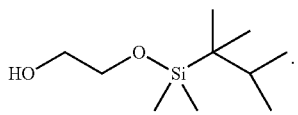
(VC)

More preferably, the 2-([trisubstituted]silyloxy) ethanol compound of formula (V) is t-butyldimethylsilyloxy ethanol (VA).

The reaction between the 2-([trisubstituted]silyloxy) ethanol compound of formula (V) and trifluoromethane sulfonic acid or an activated derivative thereof is performed in the presence of an organic base. Examples of suitable organic bases include, but not limited to, pyridine, 2,6-Lutidine, N-methylaniline, triethylamine, diisopropylamine, diisopropylethylamine and tris(2-methylpropyl) amine. Preferably, the organic base is 2,6-Lutidine.

The reaction between the 2-([trisubstituted]silyloxy) ethanol compound of formula (V) and trifluoromethane sulfonic acid or an activated derivative thereof is performed in an organic solvent. Examples of suitable organic solvents include, but are not limited to, halogenated solvents such as dichloromethane, chloroform, carbon tetrachloride; aromatic hydrocarbons such as toluene, xylene; ethers such as diethyl ether, diisopropyl ether, dimethoxyethane, tetrahydrofuran; esters such as ethyl acetate; polar aprotic solvents, such as dimethyl formamide, alkanes such as n-pentane, n-hexane or n-heptane, and any combinations and mixtures thereof. A preferred solvent is dichloromethane. A further preferred solvent is toluene.

Preferably, the compound of the general formula (IV) formed in step a) of the process of the present invention, is a compound of formula (IVA), (IVB) or (IVC):

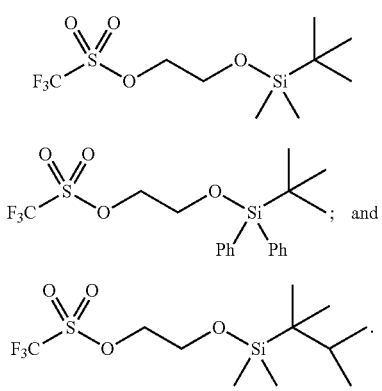

More preferably, the compound of formula (IV) is 2-(-t-butyldimethylsilyl)oxyethyl triflate (IVA).

The triflate compound of formula (IV) obtained in step a) of the process of the present invention, is an unstable compound and has been found to decompose during storage and/or during the reaction with sirolimus. This disadvantageously leads to poor product yields and hence a large molar excess of triflate of formula (IV) is charged into the reaction mixture in portions. Hence, these compounds are typically formed and used in situ.

To overcome the drawbacks of the prior art processes, the inventors have developed a process to stabilize the triflate compounds of formula (IV) by using metal salts in step b) of the process of the present invention.

In step b) of the process of the present invention sirolimus of formula (III) is mixed with a metal salt in an organic solvent. The metal salt acts as an activator and catalyzes the coupling by transmetalation and then recombination.

Examples of suitable metals include, but are not limited to, the coinage metal series comprising of aluminum, silver, magnesium, manganese, nickel, calcium, copper, gold, iron, potassium, palladium, tin, zinc and silver. Examples of suitable salts include, but are not limited to, halide, oxide, carbonate, acetate, nitrate, tosylate, hydroxide, and triflate salts.

Preferably, the metal salts used are silver salts. Silver salts are very effective as co-catalysts providing the expected coupling products. The silver salts are preferably selected from the group comprising of silver iodide, silver fluoride, silver acetate, silver nitrate, silver tosylate, silver carbonates, silver perchlorate, and silver triflate. A particularly preferred silver salt is silver acetate.

Alternatively, potassium carbonate, potassium fluoride, potassium acetate, copper acetate, magnesium salts, gold salts and the like may also be used as catalyst in step b) of the process of the present invention, with or without a stoichiometric amount of a silver salt.

The reaction rate is clearly dependent on the bulkiness at the silyl atom and on the substrate structure.

A drying agent such as sodium sulfate, calcium sulfate, calcium chloride, or molecular sieves may optionally be added in step b) to improve the product yields.

The molar ratio of the metal salt(s) to sirolimus of formula (III) preferably does not exceed 5:1, and typically is less than 3:1, and is in some aspects of the invention less than 2.5:1.

Preferably, the metal salt is added to the solution of sirolimus of formula (III) in an organic solvent. Examples of suitable solvents include, but are not limited to, halogenated solvents such as dichloromethane, chloroform, carbon tetrachloride; aromatic hydrocarbons such as toluene, xylene, benzene; ethers such as diethyl ether, diisopropyl ether, dimethoxyethane; cyclic ethers like tetrahydrofuran; esters such as ethyl acetate; polar aprotic solvents such as dimethyl formamide; alkanes such as n-pentane, n-hexane, n-heptane, and any combinations and mixtures thereof. A preferred solvent is dichloromethane. A further preferred solvent is toluene.

Preferably, the organic solvent used in step a) is the same as the solvent used in step b). More preferably, the organic solvent used in steps a) and b) is selected from toluene and dichloromethane.

In one aspect of the present invention, the triflate compound of formula (IV) is not isolated from step a). Preferably, in step c), a solution of the triflate compound of formula (IV) obtained in step a), is added into the reaction mixture obtained in step b) to obtain protected everolimus of formula (II).

In one aspect of the present invention, the triflate compound of formula (IV) is added to sirolimus solution from step b) in complete (i.e. a single addition) or portion wise (i.e. in more than one addition), preferably in about 1 to about 10 portions, more preferably in about 3 to about 5 portions.

The molar ratio of the triflate compound of formula (IV) to sirolimus of formula (III) preferably does not exceed 35:1, and typically is less than 30:1.

The reaction steps a), b) and c) of the present invention are typically carried out at a temperature in the range of from about −80° C. to about 80° C. Preferably, the reactions are carried out at a temperature in the range of from about −60° C. to about 60° C. In still other aspects, they are carried out at a temperature in the range of from about −50° C. to about 50° C.

The reaction steps a), b) and c) of the present invention are typically carried out for a time ranging from 10 minutes to 24 hours, preferably 20 minutes to 12 hours, most preferably 30 minutes to 6 hours.

The reaction steps a), b) and c) are preferably performed in the absence of light and in an inert atmosphere.

In one aspect of the present invention, there is provided a process for preparing everolimus of formula (I), which process comprises the steps of:
d) reacting a 2-([trisubstituted]silyloxy)ethanol compound of formula (V):

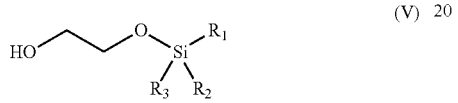

(V)

with trifluoromethane sulfonic acid or an activated derivative thereof, in the presence of a base and an organic solvent, to form a solution comprising a trisubstituted silyloxyethyltrifluoromethane sulfonate (triflate) compound of formula (IV);

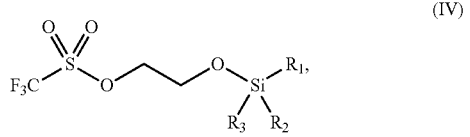

(IV)

wherein R₁, R₂ and R₃, which may be the same or different, are independently a straight or branched chain lower alkyl group and/or an aryl group;
e) reducing the volume of the solution comprising the compound of formula (IV) obtained in step d), without completely removing all of the organic solvent present;
f) reacting sirolimus of formula (III),

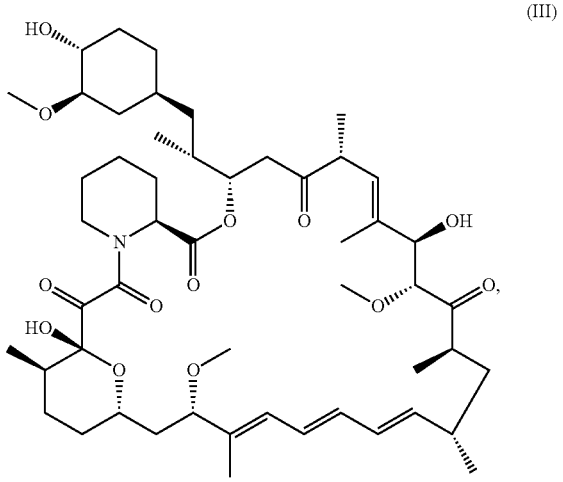 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

(III)

with the reaction mixture obtained in step e), in the presence of an organic solvent and a base to obtain protected everolimus of formula (II),

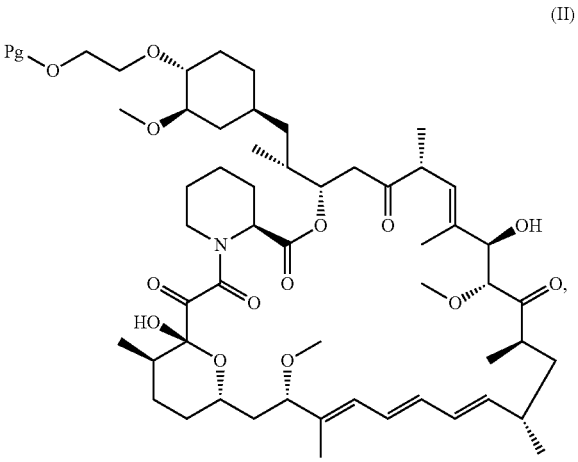

(II)

wherein, Pg is a silyl protecting group "—SiR₁R₂R₃" derived from the triflate compound of formula (IV);
g) optionally purifying the protected everolimus of formula (II); and
h) deprotecting compound (II) to obtain everolimus of formula (I).

Preferably, R₁, R₂ and R₃, which may be the same or different, are independently selected from the group consisting of a straight or branched chain C₁-C₆ alkyl group, such as methyl, ethyl, propyl, butyl, pentyl or hexyl, and/or a phenyl group.

Preferably, the 2-([trisubstituted]silyloxy)ethanol compound of formula (V) is selected from the group consisting of:
t-butyldimethylsilyloxy ethanol (VA),

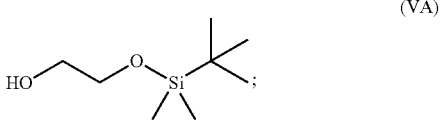

(VA)

diphenyl-tert-butylsilyloxy ethanol (VB),

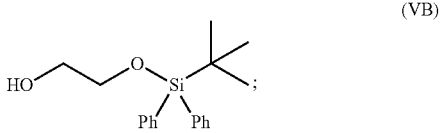 [SMILES: CC(C)(C)[Si](OCCO)(c1ccccc1)c1ccccc1]

(VB)

and
hexyldimethylsilyloxy ethanol (VC),

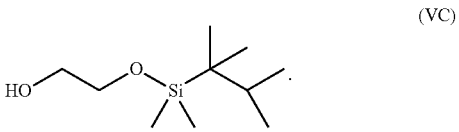

(VC)

More preferably, the 2-([trisubstituted]silyloxy) ethanol compound of formula (V) is t-butyldimethylsilyloxy ethanol (VA).

A preferred derivative of trifluoromethane sulfonic acid is trifluoromethane sulfonic anhydride.

The reaction between the 2-([trisubstituted]silyloxy) ethanol compound of formula (V) and trifluoromethane sulfonic acid or an activated derivative thereof is performed in the presence of an organic base. Examples of suitable organic bases include, but not limited to, pyridine, 2,6-Lutidine, N-methylaniline, triethylamine, diisopropylamine, diisopropylethylamine and tris(2-methylpropyl) amine. Preferably, the organic base is 2,6-Lutidine.

The reaction between the 2-([trisubstituted]silyloxy) ethanol compound of formula (V) and trifluoromethane sulfonic acid or an activated derivative thereof is performed in an organic solvent. Examples of suitable organic solvents include, but are not limited to, halogenated solvents such as dichloromethane, chloroform, carbon tetrachloride; aromatic hydrocarbons such as toluene, xylene; ethers such as diethyl ether, diisopropyl ether, dimethoxyethane; esters such as ethyl acetate; alkanes such as n-pentane, n-hexane or n-heptane, and any combinations and mixtures thereof. A particularly preferred solvent is n-heptane.

Following the reaction between the 2-([trisubstituted] silyloxy) ethanol compound of formula (V) with trifluoromethane sulfonic acid or an activated derivative thereof, the volume of the resulting solution comprising the compound of formula (IV) is reduced, without completely removing all of the organic solvent present. Preferably, the volume of organic solvent present in the reaction mixture is reduced by evaporation using known methods. More preferably, the volume of solvent present is reduced to less than 5 volumes, preferably between 1 and 3 volumes, with respect to the amount of compound of formula (V) employed. Most preferably, the volume of solvent present is reduced to about 2 volumes with respect to the amount of compound of formula (V) employed.

Preferably, the compound of formula (IV) is used without purification, i.e. is not subjected to any purification steps (e.g. flash chromatography) prior to the reaction with sirolimus of formula (III).

Sirolimus of formula (III) is mixed with the reaction mixture obtained in step e) (i.e. the solution containing the compound of formula (IV)) in the presence of a suitable solvent and a suitable base to obtain protected everolimus of formula (II), wherein, Pg is a silyl protecting group "—SiR$_1$R$_2$R$_3$" derived from the triflate compound of formula (IV).

Examples of suitable organic bases include, but not limited to, pyridine, 2,6-Lutidine, N-methylaniline, triethylamine, diisopropylamine, diisopropylethylamine and tris(2-methylpropyl) amine. Preferably, the organic base is 2,6-Lutidine.

Examples of suitable organic solvents include, but are not limited to, dichloromethane, chloroform, carbon tetrachloride, toluene, xylene, diethyl ether, diisopropyl ether, dimethoxyethane, ethyl acetate, n-pentane, n-hexane or n-heptane, and mixtures thereof. Preferably, the reaction solvent is a mixture of toluene and n-heptane.

Preferably, the reaction is carried out at a temperature in the range of from about 40° C. to about 80° C. More preferably, the reaction is carried out at a temperature in the range of from about 50° C. to about 70° C., most preferably at about 65° C.

Preferably, the reaction is carried out for a time ranging from 1 to 5 hours, preferably about 2 hours.

The compound, protected everolimus of formula (II) may, in accordance with any aspect of the process of the present invention optionally be isolated from the reaction mixture. The isolation step typically involves optionally diluting with the reaction solvent (e.g. dichloromethane and n-heptane), washing the organic layer with water followed by brine, drying, and removal of the solvent.

The crude protected everolimus of formula (II) obtained in accordance with the process of the present invention may be optionally purified in step g) using known techniques, for example by crystallization from a suitable solvent, column chromatography on a silica-packed column, etc.

Preferably, the protected everolimus of formula (II) formed in step g) is a compound of formula (IIA), (IIB) or (IIC):

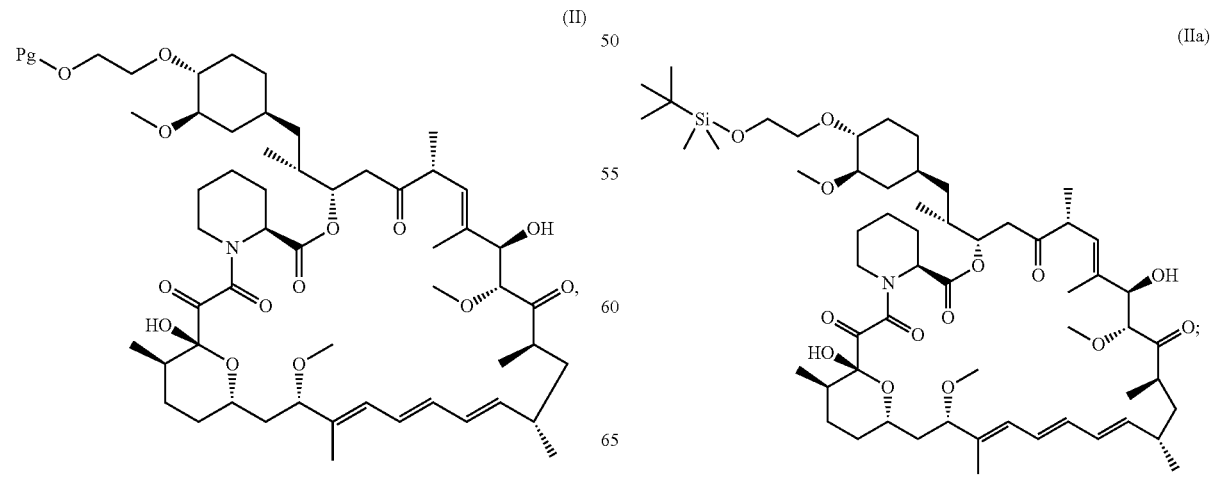

(IIb)

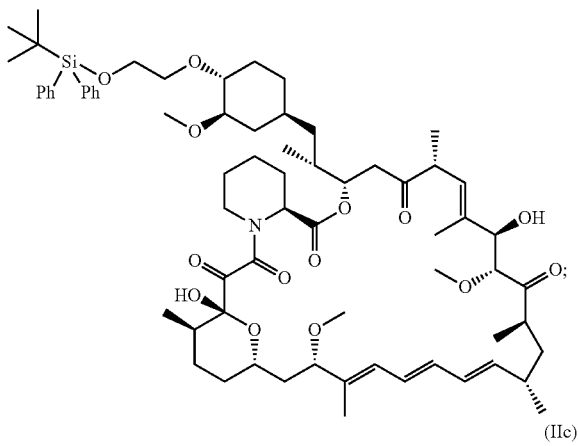

(IIc)

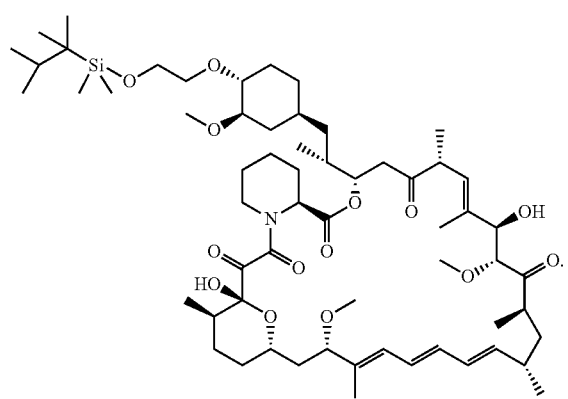

In accordance with the process of the present invention, protected everolimus of formula (II) obtained in step g) is deprotected to obtain everolimus in step h).

The deprotection step involves removal of the silyl protecting group using a suitable deprotecing agent. Suitable deprotecting agents include, but are not limited to, an acid such as a strong mineral or organic acid, preferably, hydrofluoric acid, hydrochloric acid or trifluoroacetic acid; Lewis acids such as $BF_3 \cdot Et_2O$, zinc chloride or a cationic resin, such as DIAION™ SKI110, TULSION™ T42H or UBK558.

The deprotection step is preferably performed in a suitable organic solvent, such as an aliphatic $C_1$-$C_5$ alcohol, at an ambient temperature and under inert atmosphere.

The deprotection step is preferably carried out for a time ranging from 30 minutes to 4 hours, preferably 1 hour to 2 hours.

The crude everolimus of formula (I) is preferably isolated from the reaction mixture by neutralization by a base, preferably an aqueous base, such as a solution of sodium bicarbonate, followed by extraction with a water-immiscible organic solvent, drying over a suitable drying agent and removal of the solvent.

The obtained everolimus may, optionally be purified by HPLC or lyophilization according to methods known in the art.

The 2-([trisubstituted]silyloxy)ethanol compounds of formula (V) employed in the process of the present invention may be prepared according to methods known in the art.

Optionally, the process of the present invention comprises a step in which a compound of formula (V) is prepared by reacting a silyl halide of formula, $SiR_1R_2R_3X$, wherein $R_1$-$R_3$ are as hereinbefore defined and X is a halide, with ethylene glycol in the presence of a suitable base.

Preferably, X is Cl or Br, more preferably Cl. Most preferably, the silyl halide is tert-butyldimethylsilyl chloride. A preferred base is triethylamine.

Preferably, the reaction is undertaken in the absence of a solvent. Preferably, the crude product of compound (V) is subjected to a vacuum distillation step before being reacted with trifluoromethane sulfonic acid and/or an activated derivative thereof.

In an embodiment, the present invention provides everolimus of formula (I) in substantially pure form. As used herein, "substantially pure" refers to chemical purity of greater than about 97%, preferably greater than about 98%, and more preferably greater than about preferably 99.0% by weight. Preferably, the substantially pure form of everolimus is obtainable by a process of the present invention.

The following non-limiting Examples illustrate the processes of the present invention.

EXAMPLE 1

Step 1: Preparation of Protected Everolimus (TBS-Everolimus) of Formula (IIa) Using Metal Salt, Wherein "Pg" is t-Butyldimethylsilyl t-butyldimethylsilyloxy ethanol, of formula (VA) (2.8 g, 0.016 mol) was dissolved in dichloromethane (DCM) (3 vol) and to this 2,6-Lutidine (3.50 g, 0.0327 mol) was added and the mixture was cooled to −40° C. Thereafter, trifluoromethane sulfonic anhydride (3.59 ml, 0.021 mol) was added drop-wise. The mixture was maintained at −40° C. for 30 minutes. Sirolimus (0.5 g, 0.00054 mol) was taken in another flask and dissolved in DCM (1 ml). To this sirolimus solution, silver acetate (0.018 g, 0.000109 mol) was added and cooled to −40° C. The earlier cooled triflate solution was transferred in 3 lots to the sirolimus solution maintaining temperature at −40° C. The reaction mixture was stirred at −40° C. further for 15 min before which it was slowly warmed to 0° C. and further to RT. The reaction mixture was then warmed to 40° C. and maintained at this temperature for 3 hours. The reaction was monitored by TLC. On completion of reaction, the reaction mixture was diluted with DCM and washed with water and brine. The organic layer was dried over anhydrous sodium sulphate and solvent was removed by vacuum distillation to obtain the title compound, which was directly used in the next step. HPLC product purity: 60%-85%.

Step 2: Preparation of Everolimus of Formula (I)

Protected everolimus of formula (IIa) obtained in step 1 was dissolved in methanol (10 volumes) and chilled to 0-5° C. To this solution was added drop wise, a solution of 1N HCl. The pH of the reaction was maintained between 1-3. The temperature of the reaction mixture was raised to 25° C. and stirred for 1 hour. After completion of reaction, the reaction mixture was diluted with water (15 volumes) and extracted in ethyl acetate (2×20 volumes). The organic layers were combined and washed with brine, dried over sodium sulphate. The organic layer was distilled off under reduced pressure at 30-35° C., to obtain a crude everolimus (0.8 g). The crude everolimus was further purified by preparative HPLC to yield everolimus of purity >99%.

EXAMPLE 2

Step 1: Preparation of TBS-Everolimus of Formula (IIa) without Using Metal Salt, Wherein "Pg" is t-butyldimethylsilyl t-butyldimethylsilyloxy ethanol, of formula (VA) (2.8 g, 0.016 mol) was dissolved in DCM (3 vol) and to this 2,6-Lutidine (3.50 g, 0.0327 mol) was added and the mixture was cooled to −40° C. Thereafter, trifluoromethane sulfonic anhydride (3.59 ml, 0.021 mol) was added drop-wise. The mixture was maintained at −40° C. for 30 minutes. Sirolimus (0.5 g, 0.00054 mol) was taken in another flask and dissolved in DCM (1 ml). The solution was cooled to −40° C. The earlier cooled triflate solution was transferred in 3 lots to the sirolimus solution maintaining temperature at −40° C. The reaction mixture was stirred at −40° C. further for 15 min before which it was slowly warmed to 0° C. and further to RT. The reaction mixture was then warmed to 40° C. and maintained at this temperature for 3 hours. On completion of reaction, the reaction mixture was diluted with DCM and washed with water and brine. The organic layer was dried over anhydrous sodium sulphate and solvent was removed by vacuum distillation to obtain the title compound, which was directly used in next step. HPLC purity: 10%-20%.

Step 2: Preparation of Everolimus of Formula (I)

Protected everolimus of formula (IIa) obtained in step 1 was dissolved in methanol (10 volumes) and chilled to 0-5° C. To this solution was added drop wise, a solution of 1N HCl. The pH of the reaction was maintained between 1-3. The temperature of the reaction mixture was raised to 25° C. and stirred for 1 hour. After completion of reaction, the reaction mixture was diluted with water (15 volumes) and extracted in ethyl acetate (2×20 volumes). The organic layers were combined and washed with brine, dried over sodium sulphate. The organic layer was distilled off under reduced pressure at 30-35° C., to obtain a crude everolimus which was further purified by preparative HPLC.

EXAMPLE 3

Preparation of Crude Everolimus

Step 1: Preparation of TBS-ethylene Glycol of Formula (Va)

Ethylene glycol (1.5 L, 26.58 mol) and TBDMS-Cl (485 g, 3.21 mol) were mixed together with stirring and cooled to 0° C. Triethyl amine (679 ml, 4.83 mol) was then added at 0° C. in 30-45 minutes. After addition, the reaction was stirred for 12 hours at 25-30° C. for the desired conversion. After completion of reaction, the layers were separated and the organic layer (containing TBS-ethylene glycol) was washed with water (1 L×2) and brine solution (1 L). The organic layer was then subjected to high vacuum distillation to afford 350 g of pure product.

Step 2: Preparation of TBS-glycol-Triflate of Formula (IVa)

The reaction was carried out under a nitrogen atmosphere. TBS-ethylene glycol prepared as per step 1 (85.10 g, 0.48 mol) and 2,6-Lutidine (84.28 ml, 0.72 mol) were stirred in n-heptane (425 ml) to give a clear solution which was then cooled to −15 to −25° C. Trifluoroethanesulfonic anhydride ($Tf_2O$) (99.74 ml, 0.590 mol) was added drop-wise over a period of 45 minutes to the n-heptane solution (white precipitate starts to form immediately) while maintaining the reaction at −15 to −25° C. The reaction mixture was kept at temperature between −15 to −25° C. for 2 hours. The precipitate generated was filtered off. The filtrate was then evaporated up to 2 volumes with respect to TBS-ethylene glycol (~200 ml).

Step 3: Preparation of TBS-everolimus of Formula (IIa)

30 g of sirolimus (0.0328 mol) and toluene (150 ml) were stirred together and the temperature was slowly raised to 60-65° C. At this temperature, a first portion of TBS-glycol-triflate prepared as per step 2 (100 ml) and 2,6-Lutidine (11.45 ml, 0.086 moles) were added and stirred for 40 min.

Further, a second portion of TBS-glycol-triflate (50 ml) and 2, 6-Lutidine (19.45 ml, 0.138 mol) were added and the reaction was stirred for another 40 min. This was followed by a third portion of TBS-glycol-triflate (50 ml) and 2, 6-Lutidine (19.45 ml, 0.138 mol), after which the reaction was stirred for further 90 minutes. The reaction was monitored through HPLC to check the conversion of Sirolimus to TBS-everolimus after each addition of TBS-glycol-triflate. After completion of the reaction, the reaction mixture vas diluted with n-heptane (150 ml), cooled to room temperature and stirred for another 60 minutes. The precipitated solids were filtered off and the filtrate was washed with deionized water (450 ml×4) followed by brine solution (450 ml). The filtrate was subsequently distilled off to afford TBS-everolimus (60-65 g) with 60-70% conversion from sirolimus.

Step 4: Preparation of Everolimus of Formula (I)

TBS-everolimus (65 g) obtained in step 3 was dissolved in 300 ml methanol and cooled to 0° C. 1N HCl was then added to the methanol solution (pH adjusted to 2-3) and stirred for 2 h. After completion of reaction, toluene (360 ml) and deionized water (360 ml) were added to the reaction mixture and the aqueous layer was separated. The organic layer was washed with brine solution (360 ml). The organic layer was concentrated to obtain crude everolimus (39 g) with an assay content of 30-35%, HPLC purity of 60-65%.

The crude everolimus purified by chromatography to achieve purity more than 99%.

The invention claimed is:
1. A process for preparing everolimus of formula (I):

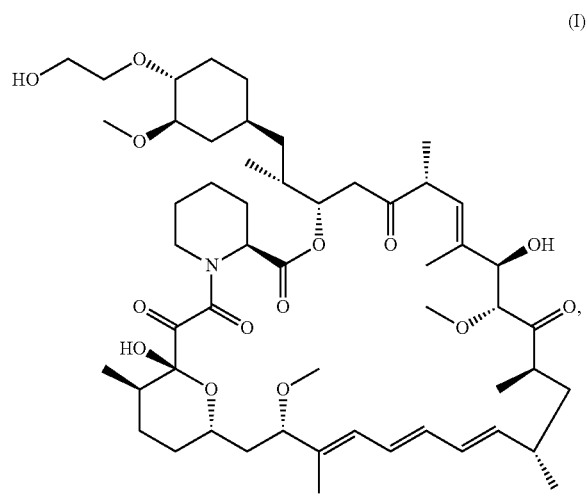 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

(I)

which process comprises the steps of:
either,
a) reacting a 2-([trisubstituted]silyloxy)ethanol compound of formula (V):

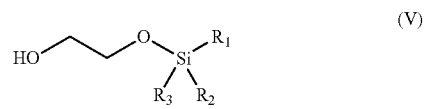

(V)

with trifluoromethane sulfonic acid or an activated derivative thereof, in the presence of a base and an organic solvent, to form a trisubstituted silyloxyethyltrifluoromethane sulfonate (triflate) compound of formula (IV):

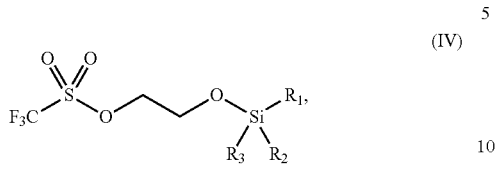

wherein $R_1$, $R_2$ and $R_3$, which may be the same or different, are independently a straight or branched chain lower alkyl group and/or an aryl group;

b) mixing sirolimus of formula (III):

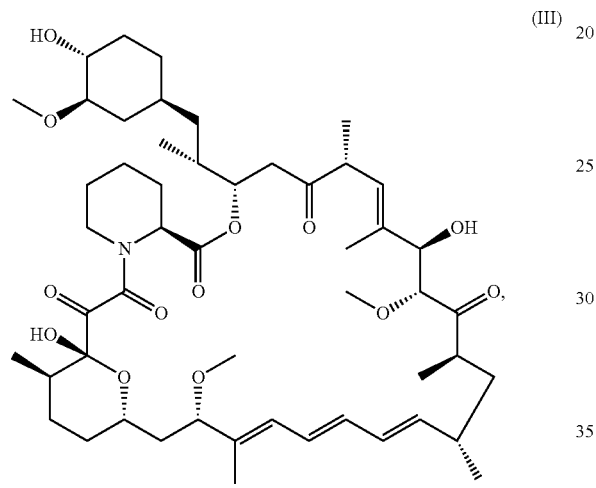

with a metal salt in an organic solvent; and c) admixing the solution containing the triflate compound of formula (IV) obtained in step a) with the reaction mixture obtained in step b) to obtain protected everolimus of formula (II),

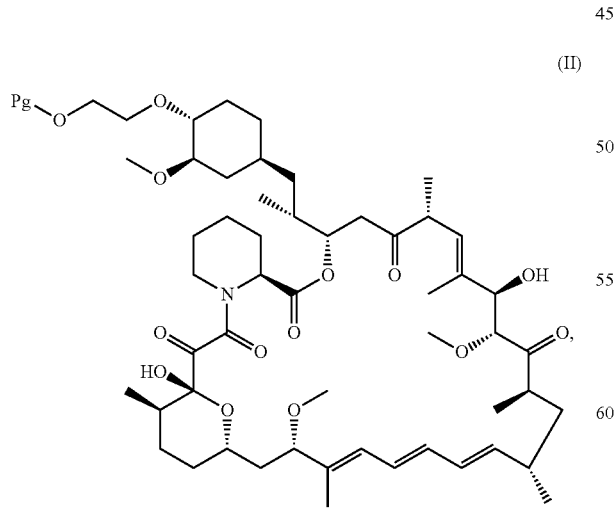

wherein, Pg is a silyl protecting group —$SiR_1R_2R_3$ derived from the triflate compound of formula (IV);

or, d) reacting a 2-([trisubstituted]silyloxy)ethanol compound of formula (V):

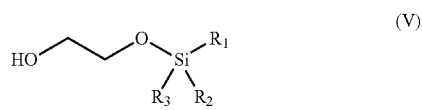

with trifluoromethane sulfonic acid or an activated derivative thereof, in the presence of a base and an organic solvent, to form a solution comprising a trisubstituted silyloxyethyltrifluoromethane sulfonate (triflate) compound of formula (IV):

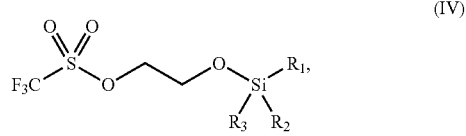

wherein $R_1$, $R_2$ and $R_3$, which may be the same or different, are independently a straight or branched chain lower alkyl group and an aryl group;

e) reducing the volume of the solution comprising the compound of formula (IV) obtained in step d), without completely removing all of the organic solvent present;

f) reacting sirolimus of formula (III):

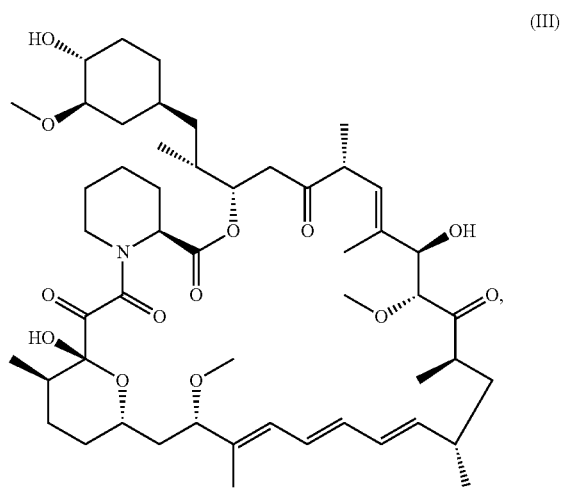 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

with the reaction mixture obtained in step e), in the presence of an organic solvent and a base to obtain protected everolimus of formula (II):

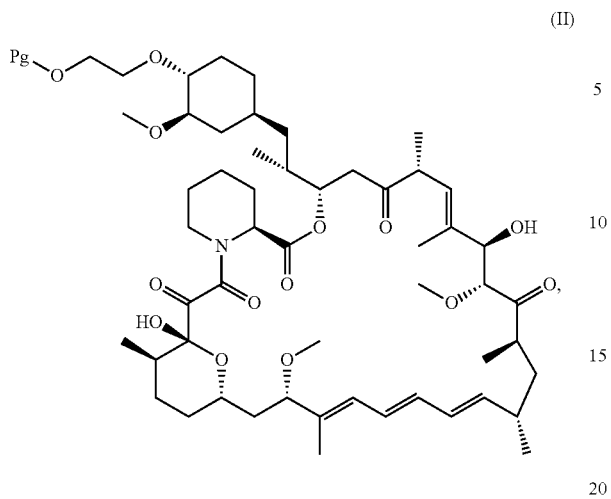

(II)

wherein, Pg is a silyl protecting group —SiR$_1$R$_2$R$_3$ derived from the triflate compound of formula (IV);

and following step c) or step f), g) optionally purifying the protected everolimus of formula (II); and h) deprotecting compound (II) to obtain everolimus of formula (I).

2. The process for preparing everolimus according to claim 1, comprising the following steps:

d) reacting a 2-([trisubstituted]silyloxy)ethanol compound of formula (V):

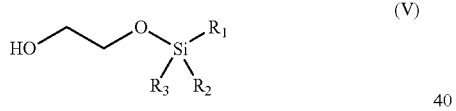

(V)

with trifluoromethane sulfonic acid or an activated derivative thereof, in the presence of a base and an organic solvent, to form a solution comprising a trisubstituted silyloxyethyltrifluoromethane sulfonate (triflate) compound of formula (IV):

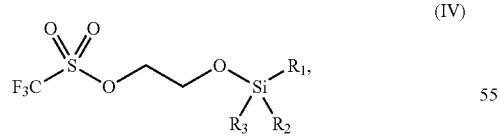

(IV)

wherein R$_1$, R$_2$ and R$_3$, which may be the same or different, are independently a straight or branched chain lower alkyl group and/or an aryl group;

e) reducing the volume of the solution comprising the compound of formula (IV) obtained in step d), without completely removing all of the organic solvent present;

reacting sirolimus of formula (III):

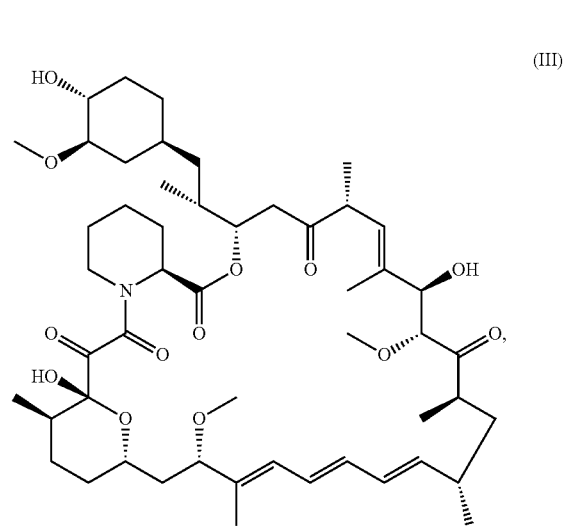

(III)

with the reaction mixture obtained in step e), in the presence of an organic solvent and a base to obtain protected everolimus of formula (II):

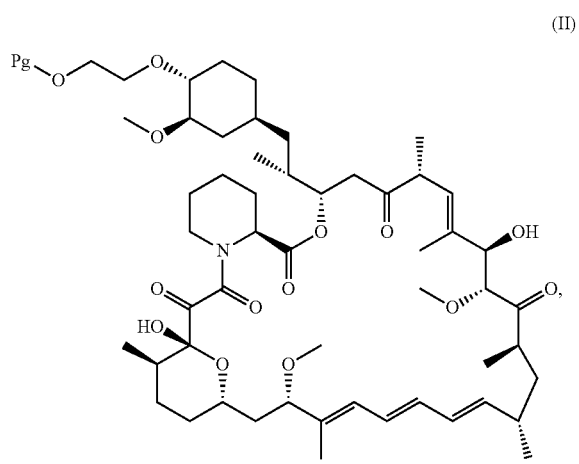

(II)

wherein, Pg is a silyl protecting group —SiR$_1$R$_2$R$_3$ derived from the triflate compound of formula (IV);

g) optionally purifying the protected everolimus of formula (II); and h) deprotecting compound (II) to obtain everolimus of formula (I).

3. The process for preparing everolimus according to claim 1, comprising the following steps:

a) reacting a 2-([trisubstituted]silyloxy)ethanol compound of formula (V):

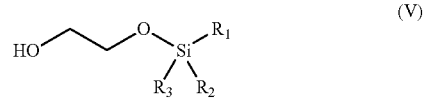

(V)

with trifluoromethane sulfonic acid or an activated derivative thereof, in the presence of a base and an organic solvent, to form a trisubstituted silyloxyethyltrifluoromethane sulfonate (triflate) compound of formula (IV):

(IV)

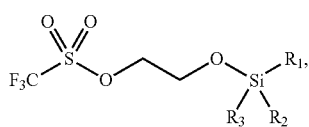

wherein R₁, R₂ and R₃, which may be the same or different, are independently a straight or branched chain lower alkyl group and/or an aryl group;
b) mixing sirolimus of formula (III):

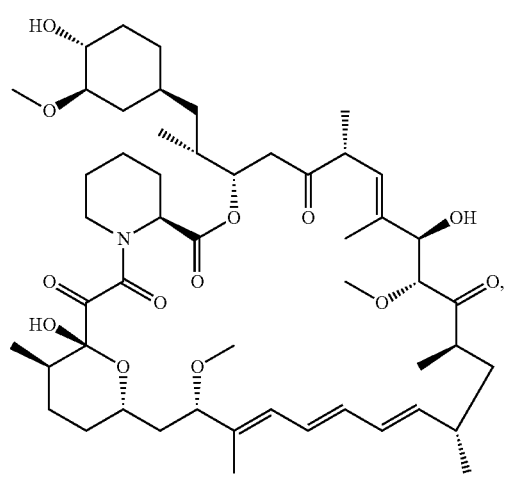

(III)

with a metal salt in an organic solvent; and
c) admixing the solution containing the triflate compound of formula (IV) obtained in step a) with the reaction mixture obtained in step b) to obtain protected everolimus of formula (II),

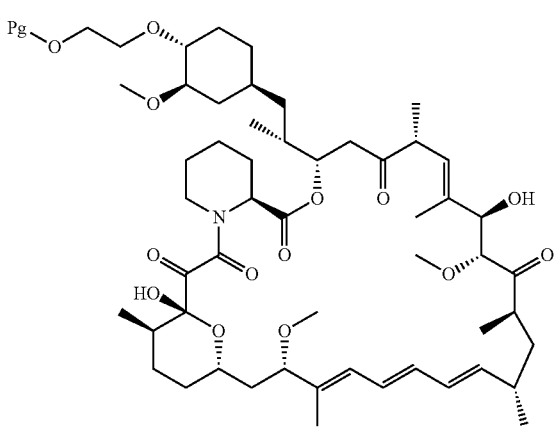

(II)

wherein, Pg is a silyl protecting group —SiR₁R₂R₃ derived from the triflate compound of formula (IV);
g) optionally purifying the protected everolimus of formula (II); and
h) deprotecting compound (II) to obtain everolimus of formula (I).

4. The process according to claim 1, wherein the 2-([tri-substituted]silyloxy)ethanol compound of formula (V) is selected from the group consisting of:

t-butyldimethylsilyloxy ethanol (VA),

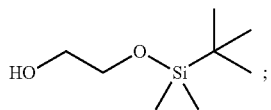

(VA)

diphenyl-tert-butylsilyloxy ethanol (VB),

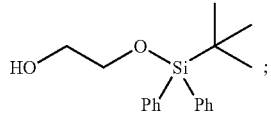

(VB)

and
hexyldimethylsilyloxy ethanol (VC),

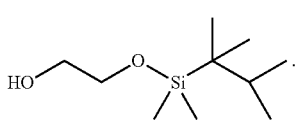

(VC)

5. The process according to claim 4, wherein the 2-([tri-substituted]silyloxy) ethanol compound of formula (V) is t-butyldimethylsilyloxy ethanol (VA).

6. The process according to claim 1, wherein the base is selected from pyridine, 2,6-Lutidine, N-methylaniline, triethylamine, diisopropylamine, diisopropylethylamine and tris(2-methylpropyl) amine.

7. The process according to claim 1, wherein the 2-([tri-substituted]silyloxy)ethanol compound of formula (V) is reacted with trifluoromethane sulfonic anhydride to form a trisubstituted silyloxyethyltrifluoromethane sulfonate (triflate) compound of formula (IV).

8. The process according to claim 1, wherein the protected everolimus of formula (II) is purified before the deprotection step.

9. The process according to claim 1, wherein the protected everolimus of formula (II) is deprotected using a strong mineral acid, an organic acid, a Lewis acid or a cationic resin, to obtain everolimus.

10. The process according to claim 1, wherein the metal salt comprises a metal ion selected from aluminum, magnesium, manganese, nickel, calcium, copper, gold, iron, potassium, palladium, tin, zinc and silver.

11. The process according to claim 10, wherein the salt is selected from the group consisting of a halide, oxide, carbonate, acetate, nitrate, tosylate, hydroxide and triflate salt.

12. The process according to claim 11, wherein the salt is a silver salt selected from the group consisting of silver iodide, silver fluoride, silver acetate, silver nitrate, silver tosylate, silver carbonate, silver perchlorate and silver triflate.

13. The process according to claim 1, wherein the molar ratio of the metal salt to sirolimus of formula (II) does not exceed 5:1.

14. The process according to claim 1, wherein the organic solvent in step a) and/or step b) is selected from dichloromethane, chloroform, carbon tetrachloride, toluene, xylene, benzene, diethyl ether, diisopropyl ether, dimethoxyethane, tetrahydrofuran, ethyl acetate, dimethyl formamide, n-pentane, n-hexane, n-heptane and mixtures thereof.

15. The process according to claim 1, wherein the organic solvent in step d) and/or step f) is selected from dichloromethane, chloroform, carbon tetrachloride, toluene, xylene, diethyl ether, diisopropyl ether, dimethoxyethane, ethyl acetate, n-pentane, n-hexane or n-heptane, and mixtures thereof.

16. The process according to claim 1, wherein the volume of the solution comprising the compound of formula (IV) obtained in step d) is reduced to less than 5 volumes with respect to the amount of compound of formula (V) employed.

17. The process according to claim 1, wherein the volume of the solution comprising the compound of formula (IV) obtained in step d) is reduced to about 2 volumes with respect to the amount of compound of formula (V) employed.

18. The process according to claim 1, wherein in step d) the compound of formula (IV) is used without purification prior to the reaction with sirolimus of formula (III).

19. The process according to claim 1, wherein step f) is carried out at a temperature in the range from about 40° C. to about 80° C.

20. The process according to claim 1, wherein the 2-([tri-substituted]silyloxy)ethanol compound of formula (V) is prepared by reacting a silyl halide of formula, $SiR_1R_2R_3X$, wherein $R_1$-$R_3$ are as defined in claim 1 and X is a halide, with ethylene glycol in the presence of a base.

21. The process according to claim 20 wherein the base is triethylamine.

* * * * *